US009301858B2

(12) United States Patent
Barsoum et al.

(10) Patent No.: US 9,301,858 B2
(45) Date of Patent: Apr. 5, 2016

(54) APPARATUS AND METHOD FOR AIDING VISUALIZATION AND/OR PLACING A LANDMARK DURING A SURGICAL PROCEDURE

(71) Applicant: THE CLEVELAND CLINIC FOUNDATION, Cleveland, OH (US)

(72) Inventors: Wael K. Barsoum, Bay Village, OH (US); Jason A. Bryan, Avon Lake, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 239 days.

(21) Appl. No.: 14/186,092

(22) Filed: Feb. 21, 2014

(65) Prior Publication Data

US 2014/0236160 A1    Aug. 21, 2014

Related U.S. Application Data

(60) Provisional application No. 61/767,319, filed on Feb. 21, 2013.

(51) Int. Cl.
| | |
|---|---|
| A61F 2/46 | (2006.01) |
| A61B 17/17 | (2006.01) |
| A61B 17/56 | (2006.01) |
| A61B 17/90 | (2006.01) |
| A61F 2/34 | (2006.01) |
| A61F 2/30 | (2006.01) |

(52) U.S. Cl.
CPC ............ *A61F 2/4657* (2013.01); *A61B 17/1742* (2013.01); *A61B 17/1746* (2013.01); *A61B 17/56* (2013.01); *A61F 2/4684* (2013.01); *A61B 2017/564* (2013.01); *A61B 2017/90* (2013.01); *A61F 2/34* (2013.01); *A61F 2002/30616* (2013.01); *A61F 2002/30617* (2013.01)

(58) Field of Classification Search
CPC ............... A61B 17/17; A61B 17/1742; A61B 17/1746; A61B 17/56; A61B 2017/564; A61B 17/88; A61B 2017/90; A61F 2/4657; A61F 2/4684
See application file for complete search history.

(56) References Cited

U.S. PATENT DOCUMENTS

| | | | |
|---|---|---|---|
| 4,528,980 A | 7/1985 | Kenna | |
| 7,828,806 B2 | 11/2010 | Graf et al. | |
| 8,469,962 B1 * | 6/2013 | Head | A61B 17/1746 606/91 |
| 8,763,268 B2 * | 7/2014 | Iannotti | A61B 17/17 33/638 |
| 2006/0058886 A1 | 3/2006 | Wozencroft | |
| 2011/0190775 A1 | 8/2011 | Ure | |
| 2012/0245647 A1 | 9/2012 | Kunz et al. | |
| 2014/0163564 A1 * | 6/2014 | Bollinger | A61B 17/1666 606/91 |

* cited by examiner

*Primary Examiner* — Larry E Waggle, Jr.
(74) *Attorney, Agent, or Firm* — Tarolli, Sundheim, Covell & Tummino LLP

(57) ABSTRACT

An apparatus for aiding visualization of a prosthetic implant and concurrently landmarking a patient tissue includes a center post having proximal and distal post ends longitudinally separated by a post body. The post body defines a post axis coaxially therewith. An implant emulator embodies a reference feature of a prosthetic implant. The implant emulator is carried on an outer surface of the center post at a predetermined longitudinal spacing from the distal post end. A guiding device is removably attached to the implant emulator. The guiding device includes an attachment structure attached to the implant emulator. A spacing arm is connected to the attachment structure and extends laterally outward from the post axis. A landmark guiding structure is connected to the spacing arm, spaced apart from the center post, and embodies at least one of a location and a trajectory for placement of a landmark.

40 Claims, 9 Drawing Sheets

… (1)

APPARATUS AND METHOD FOR AIDING VISUALIZATION AND/OR PLACING A LANDMARK DURING A SURGICAL PROCEDURE

RELATED APPLICATION

This application claims priority from U.S. Provisional Application No. 61/767,319, filed 21 Feb. 2013, the subject matter of which is incorporated herein by reference in its entirety.

TECHNICAL FIELD

The present invention relates to an apparatus and method for aiding visualization and/or placing a landmark during a surgical procedure and, more particularly, to a method and apparatus for aiding visualization of a prosthetic implant and concurrently landmarking a patient tissue during a patient procedure.

BACKGROUND OF THE INVENTION

In the installation of a prosthetic hip joint into a patient's body, an acetabular component (usually a cup) is implanted into the acetabulum of the patient's pelvis. An obverse surface of the acetabular component is configured for articulating contact with a femoral component carried by the patient's femur. A reverse surface of the acetabular component is secured to the bone surface of the acetabulum.

Because the hip prosthesis is normally provided to correct a congenital or acquired defect of the native hip joint, the acetabulum often exhibits a pathologic, nonstandard anatomic configuration. A surgeon must compensate for such pathologic acetabular anatomy when implanting the acetabular component in striving to achieve a solid anchoring of the acetabular component into the acetabulum. Detailed preoperative planning, using two- or three-dimensional internal images of the hip joint, often assists the surgeon in compensating for the patient's anatomical limitations. Additionally, during a surgical procedure, it may be useful for the surgeon to be able to easily visualize a "final" placement of a prosthetic component with respect to the patient tissue.

During the surgery, an elongated pin may be inserted into the surface of the patient's bone, at a predetermined trajectory and location, to act as a passive landmark or active guiding structure in carrying out the preoperatively planned implantation. This "guide pin" may remain as a portion of the implanted prosthetic joint or may be removed before the surgery is concluded. This type of pin-guided installation is common in any joint replacement procedure—indeed, in any type of surgical procedure in which a surgeon-placed fixed landmark is desirable.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. Again, a guide pin may be temporarily or permanently placed into the exposed bone surface to help orient the surgeon and thereby enhance the accuracy and efficiency of the surgical procedure.

A carefully placed guide pin or other landmark, regardless of the reason provided, will reduce the need for intraoperative imaging in most surgical procedures and should result in decreased operative time and increased positional accuracy, all of which are desirable in striving toward a positive patient outcome.

SUMMARY OF THE INVENTION

In an embodiment of the present invention, an apparatus for aiding visualization of a prosthetic implant and concurrently landmarking a patient tissue is described. A center post has proximal and distal post ends longitudinally separated by a post body. The post body defines a post axis coaxially therewith. An implant emulator embodies a reference feature of a prosthetic implant. The implant emulator is carried on an outer surface of the center post at a predetermined longitudinal spacing from the distal post end. A guiding device is removably attached to the implant emulator. The guiding device includes an attachment structure attached to the implant emulator. A spacing arm is connected to the attachment structure and extends laterally outward from the post axis. A landmark guiding structure is connected to the spacing arm, spaced apart from the center post, and embodies at least one of a location and a trajectory for placement of a landmark.

In an embodiment of the present invention, an apparatus for trialing a portion of an acetabular cup and concurrently placing at least one landmark at an acetabular surgical site is described. A center post has proximal and distal post ends longitudinally separated by a post body. The post body defines a post axis coaxially therewith. A cup emulator represents only a rim portion of an acetabular cup. The cup emulator is carried on an outer surface of the center post at a predetermined longitudinal spacing from the distal post end. The cup emulator is coaxial with the post axis. A pin guide is removably attached to the cup emulator. The pin guide includes an attachment structure attached to the cup emulator. A spacing arm is connected to the attachment structure and extends laterally outward from the post axis. A pin guiding bore is connected to the spacing arm, spaced apart from the center post, and embodies at least one of a location and a trajectory for placement of a landmark with respect to the center post and the cup emulator.

In an embodiment of the present invention, a method of aiding visualization of a prosthetic implant and concurrently landmarking the surgical site is provided. A device is provided, the device comprising a center post having proximal and distal post ends longitudinally separated by a post body. The post body defines a post axis coaxially therewith. An implant emulator embodies a reference feature of a prosthetic implant. The implant emulator is carried on an outer surface of the center post at a predetermined longitudinal spacing from the distal post end. A guiding device is removably attached to the implant emulator. The guiding device includes an attachment structure attached to the implant emulator. A spacing arm is connected to the attachment structure and extends laterally outward from the post axis. A landmark guiding structure is connected to the spacing arm, spaced apart from the center post, and embodies at least one of a location and a trajectory for placement of a landmark. The distal post end is placed in contact with a patient tissue at the surgical site. A position of the implant emulator with respect to the patient tissue is adjusted. The implant emulator is placed in a desired visualization position with respect to the patient tissue. With the implant emulator maintained in the desired visualization position, a landmark is placed into at least one of a desired landmark location and a desired landmark trajectory with respect to the patient tissue with the aid of at least one of the post lumen and the landmark guiding structure.

BRIEF DESCRIPTION OF THE DRAWINGS

For a better understanding of the invention, reference may be made to the accompanying drawings, in which.

DESCRIPTION OF EMBODIMENTS

Figure 1:
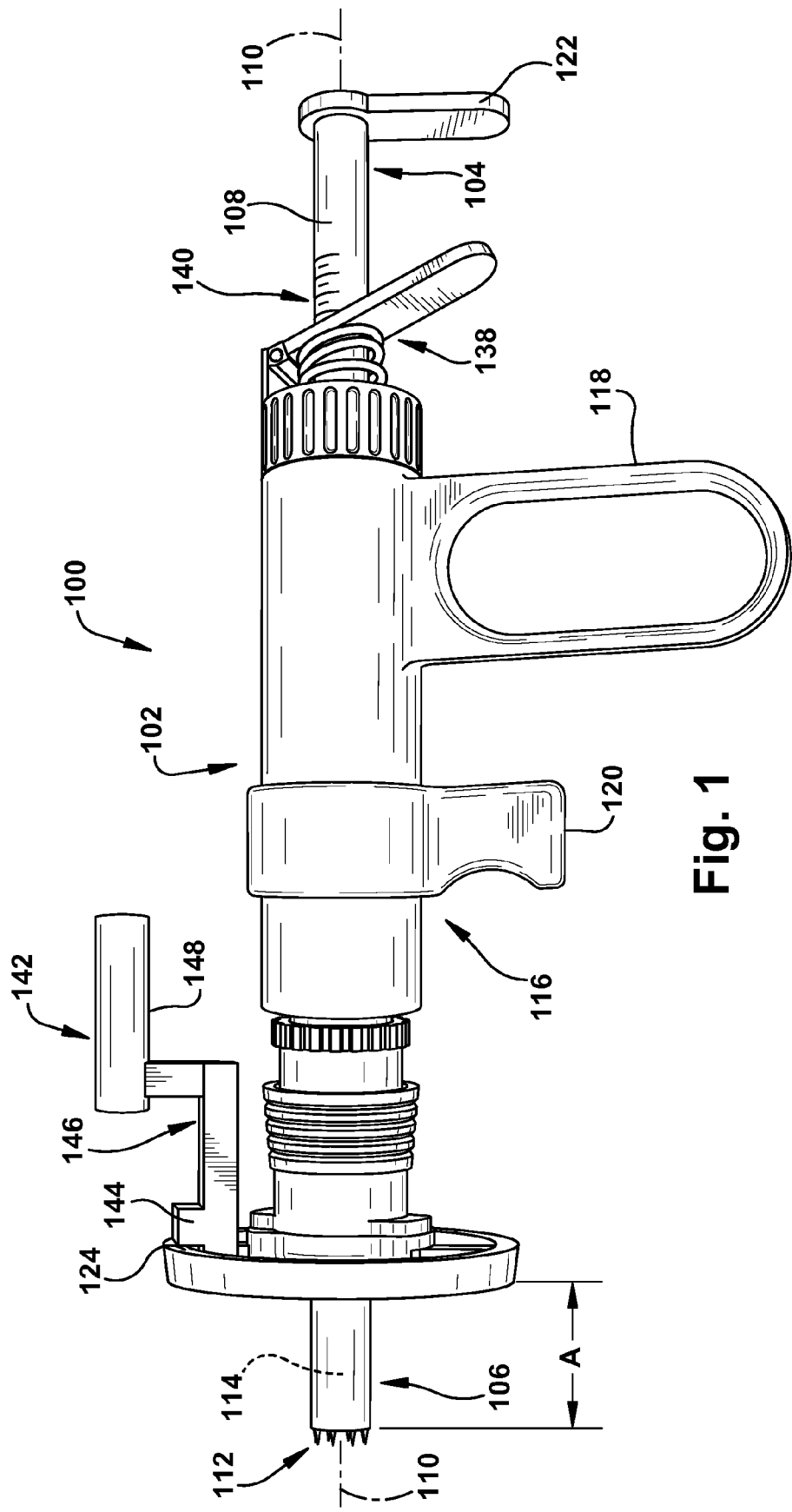
FIG. 1 is a side view of one embodiment of the present invention.

In accordance with the present invention, FIG. 1 depicts an apparatus 100 for aiding visualization of a prosthetic implant and concurrently landmarking a patient tissue. The apparatus 100 includes a center post 102 having proximal and distal post ends 104 and 106, respectively, longitudinally separated by a post body 108. The post body 108 defines a post axis 110 coaxially therewith. Optionally, the distal post end 106 may include at least one tissue-engaging feature 112, such as the teeth or spikes shown in the Figures, to help prevent the distal post end from sliding along a patient tissue. The post body 108 may include a post lumen 114 extending longitudinally therethrough between the proximal and distal post ends 104 and 106, coaxially with the post axis 110.

As shown in FIG. 1, a tubular housing 116 may at least partially laterally surround the post body 108. The housing 116 may be provided for any reason, including protection and/or manipulability of the of the center post 102. For example, when the housing 116 is used to help a user manipulate the center post 102, a grip 118 and/or trigger post 120 may be provided to assist the user with holding the center post 102 in a pistol-type gripping posture.

Optionally, a key 122 may be provided on the center post 102, such as at the proximal post end 104 as shown in FIG. 1. When present, the key 122 may be used to rotationally manipulate the center post 102, indicate a rotational orientation of the center post, provide a "stop" function to limit another structure's longitudinal motion with respect to the apparatus 100, or for any other reason.

An implant emulator 124, depicted in FIG. 1, may be provided to the apparatus 100 to embody a reference feature of a prosthetic implant. The term "emulator" is used herein to indicate a structure used with the apparatus 100 which imitates at least a portion of another "model" structure which is not directly used with the apparatus concurrently with the emulator. The term "reference feature" is used herein to indicate a dimension, physical configuration, or other feature of interest of the model structure. For example, the physical structure of the depicted implant emulator 124 imitates or represents (but does not necessarily exactly duplicate) a reference feature that is a rim of an acetabular cup implant. The substantially circular implant emulator 124 shown emulates a footprint, silhouette, and/or significant dimension of the acetabular cup implant to help the user envision how that reference feature (here, the implant rim) will interact and/or relate to the patient tissue. The term "significant dimension" is used herein to indicate some physical property or measurement of a structure that is of particular interest to a user of the apparatus 100. For example, a maximum diameter and/or maximum depth of an acetabular cup implant could each be a significant dimension to the user during the same or different phases of the implantation surgery. As another example, a center of rotation and/or implant length may be a significant dimension for a femoral or humeral implant.

The patient tissue is shown and described herein as an acetabulum, but the patient tissue could be any desired types such as, but not limited to, hip joints, shoulder joints, knee joints, ankle joints, phalangeal joints, metatarsal joints, spinal structures, long bones, soft tissue, or any other suitable use environment for the present invention. Likewise, the prosthetic implant is described herein as an acetabular cup, but could be any permanently, semi-permanently, and/or temporarily installed non-native structure used to supplement and/or supplant the function of any desired type of native or previously altered patient tissue.

The emulation function of the implant emulator 124 may be assisted for some visualization use environments of the present invention by a direct correlation between the shape of the implant emulator and the reference feature of the model structure. However, it is contemplated that, even in those particular visualization use environments, the size of the implant emulator 124 may be scaled differently from the size of the reference feature of the model structure. For example, a specific implant emulator 124 might represent a rim of an acetabular cup by having a substantial correlation in shape with that cup rim, but the implant emulator could be scaled down from the actual size of the cup rim (e.g., 90% scale) so that the implant emulator 124 could be used by a surgeon to visualize a final installed position of the cup rim even if the acetabulum is still in a "native state" before any planned or anticipated intraoperative reaming procedure has taken place. In some embodiments, however, at least a portion of the implant emulator 124 could be substantially similar in size and/or shape to at least a corresponding portion of the implant being emulated, as desired for a particular use environment of the present invention.

The implant emulator 124 is carried on an outer surface of the center post 102 and is at a predetermined longitudinal spacing from the distal post end 106. For example, and as shown in FIG. 1, the implant emulator 124 could be a relatively planar construct extending substantially laterally from the post axis 110 at a distance "A" from the distal post end 106. Optionally, and especially in situations when the implant emulator 124 has some rotational symmetry in the lateral plane, the implant emulator could be coaxial with the post axis 110 so that the implant emulator is "centered around" the post axis. However, when the implant emulator 124 is not substantially planar, any desired feature of the implant emulator can be used as a reference point for the longitudinal spacing.

It is contemplated that the combination of a significant dimension of the implant emulator 124 and the predetermined longitudinal spacing ("A", in FIG. 1) could correspond directly to a significant dimension and a longitudinal measurement of an available prosthetic implant. The term "significant dimension" is used herein to indicate a one-, two-, or three-dimensional size, shape, or other physical property of the prosthetic implant that is of interest to the user of the apparatus 100, especially when that "significant dimension" contributes to the user's being able to visualize, with the aid of the apparatus, what the prosthetic implant would look like when placed in a predetermined relationship with the patient tissue. For example, if the prosthetic implant is an acetabular cup, the significant dimension of the implant emulator 124 could be an outer diameter corresponding to the cup rim, and the predetermined longitudinal spacing could correspond to a depth of the cup (i.e., a longitudinal distance, or radius, between the rim and a point on the substantially-hemispherical cup body which is at a maximum longitudinal spacing from the rim). In this manner, the approximate outer dimensions of the prosthetic implant can be represented by the shape of the implant emulator 124 and the position of the implant emulator along the center post 102.

In some use environments, it may be desirable for the implant emulator 124 to be selectively longitudinally movable with respect to the center post 102. For example, if the combination of the shape of the implant emulator 124 and the position of the implant emulator along the center post 102 are used to represent or refer to the diameter and depth, respectively, of a specific acetabular cup, the user may wish to adjust the apparatus 100 to represent a different acetabular cup having a different depth and/or diameter. In the depicted apparatus 100, the implant emulator 124 is removably connected to the center post 102 via a coupling mechanism 226, shown in FIG. 2.

Figure 2:
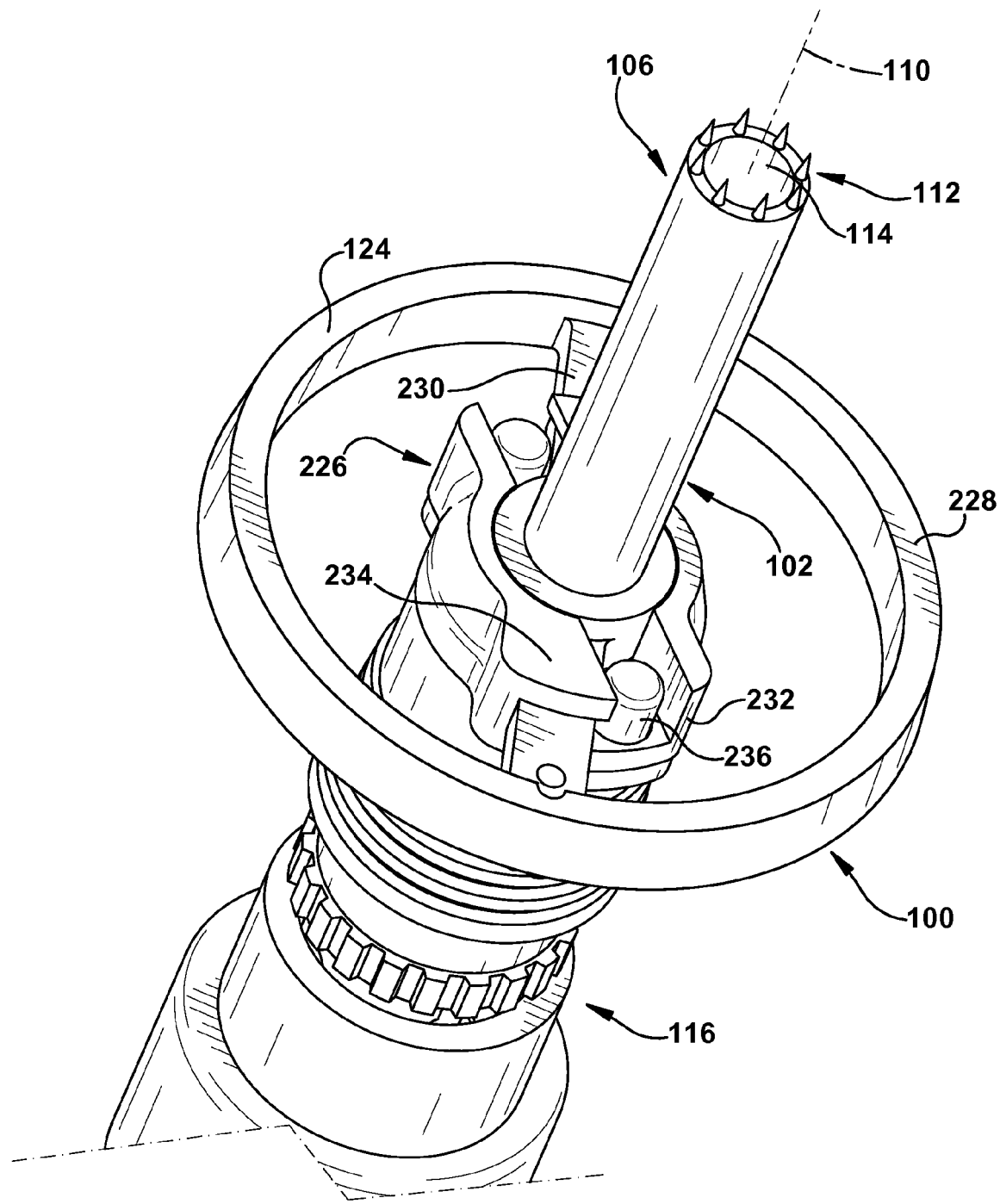
FIG. 2 is a partial perspective bottom view of the embodiment of FIG. 1.
Figure 3:
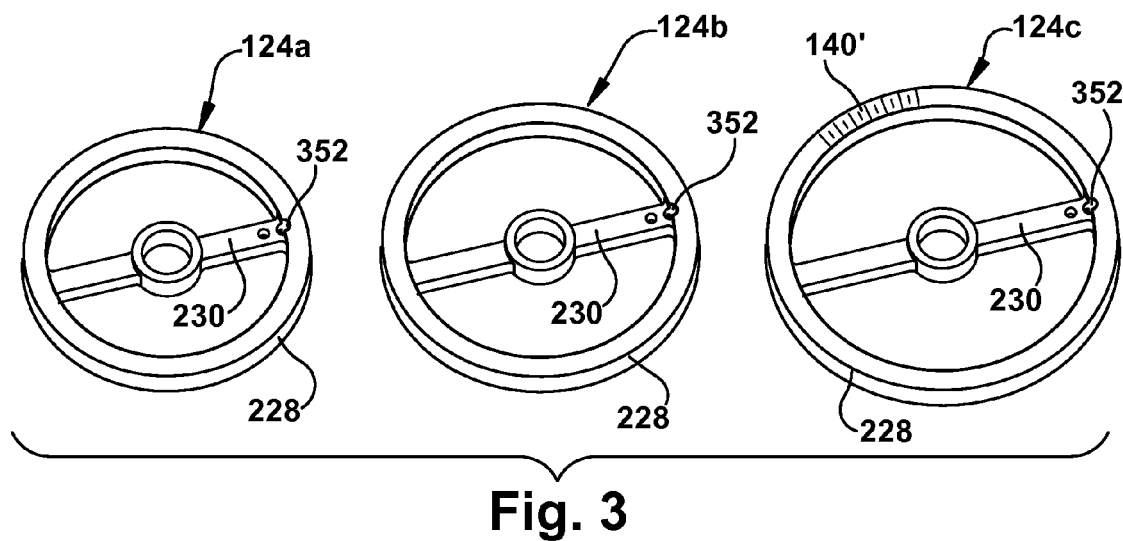
FIG. 3 is a top view of several optional configurations for a component of the embodiment of FIG. 1.

More specifically, and as is especially apparent in FIGS. 2 and 3, the implant emulator 124 shown includes a rim ring 228 representing a reference feature that is a rim of an acetabular cup. An emulator crossbar 230 may span the rim ring 228, optionally across a full diameter thereof, though it is contemplated that the emulator crossbar could instead span a chord of the rim ring for visualization offset from the center post 102. As shown in FIG. 2, the housing 116 includes a coupling mechanism 226 which allows entry thereinto of the emulator crossbar 230 via a coupler channel 232, then the implant emulator 124 can be rotated a short distance clockwise (in the orientation of FIG. 2) about the post axis 110 until the emulator crossbar 230 passes under a coupler overhang 234 that prevents longitudinal motion of the implant emulator 124. In FIG. 2, only one lateral side of the coupling mechanism 226 is visible, with the other lateral side of the coupling mechanism being blocked from view in this Figure by the center post 102.

Optionally, one or more coupler posts 236, which could be automatically (e.g., spring-biased) or manually (e.g., via a manipulable collar) retractable into a lower surface of the coupler channel 232, could become located in the coupler channel to substantially block rotation of the "connected" emulator crossbar 230 back into the coupler channel until the user wishes to remove the implant emulator 124 from the remaining structure(s) of the apparatus 100. While one example coupling mechanism 226 is shown and described herein, one of ordinary skill in the art will be able to provide a permanent or removable coupling scheme to connect a chosen implant emulator 124 to a center post 102 in a desired manner.

In the embodiment shown in the Figures, the coupling mechanism 226 is carried on the housing 116. Since the center post 102 is longitudinally movable with respect to the housing 116, this commutation property means that the coupling mechanism 226 is also longitudinally movable with respect to the center post 102. Accordingly, the predetermined longitudinal distance "A" between the distal post end 106 and the implant emulator 124 can be changed through manipulation of the housing 116 to move the coupling mechanism 226 (holding the implant emulator 124) along the center post 102.

Optionally, a feature of the apparatus 100 may be configured to place the implant emulator 124 at a desired longitudinal spacing along the center post 102 and/or maintain the implant simulator in that desired spacing. As is visible in FIG. 1, a spring biased pivot member 138 can be operated in a "wedge" type manner to prevent or allow movement of the housing 116 with respect to the center post 102, but one of ordinary skill in the art can readily provide the apparatus 100 with a suitable feature for creation and/or maintenance of the longitudinal spacing of the implant emulator 124 with respect to the distal post end 106.

With reference to FIG. 3, a plurality of implant emulators 124a, 124b, 124c, each differing in at least one significant dimension from one another, may be provided. For example, the plurality of implant emulators 124a, 124b, 124c may have substantially the same physical configuration but differ in scale from each other, such as those shown in FIG. 3 which each represent a different "cup size" (rim diameter as the significant dimension) acetabular cup implant. It is also contemplated that an adjustable implant emulator (not shown) could be used to represent a plurality of different implants when suitably adjusted.

More specifically, when a plurality of implant emulators 124 are provided, a first implant emulator (124a, for example) can be initially connected to the center post 102 via the coupling mechanism 226, then the coupling mechanism is manipulated to release the first implant emulator 124a and removably connect a second implant emulator (124b, for example) to the center post 102 in place of the first implant emulator 124a. Accordingly, a user can, through sequential use of multiple implant emulators 124a, 124b, 124c with the apparatus 100, perform a "trialing" procedure to sequentially visualize the reference features (here, the rims) of different sizes of acetabular cups in a particular patient tissue environment with the aid of the apparatus 100.

Similarly, the coupling mechanism 226 can be moved longitudinally along the center post 102 to simulate or reflect a depth (longitudinal measurement) of a particular implant (here, an acetabular cup). For example, the leftmost implant emulator 124a of FIG. 3 has a diameter corresponding to a reference feature of a smaller acetabular cup than the larger-diameter rightmost implant emulator 124c in that Figure. Generally, a smaller-diameter acetabular cup will be shallower than a larger-diameter acetabular cup, so when the leftmost implant emulator 124a is being used with the apparatus 100, the longitudinal distance between that implant emulator and the distal post end 106 will normally be smaller than a corresponding longitudinal distance for the rightmost implant emulator 124c, to assist the user with accurately visualizing the longitudinal component of the implant being emulated. Optionally, the position of the implant emulator 124 with respect to the center post 102 may be at least partially established and/or indicated through the use of a graduated scale 140 to aid the user in accurately and/or reproducibly longitudinally locating the implant emulator 124 with respect to the distal post end 106.

Again with reference to FIG. 1, a guiding device 142 may be removably attached to any suitable structure of the apparatus 100, such as the implant emulator 124. The guiding device 142 includes an attachment structure 144 attached to the implant emulator 124 or another structure of the apparatus

Figure 4:
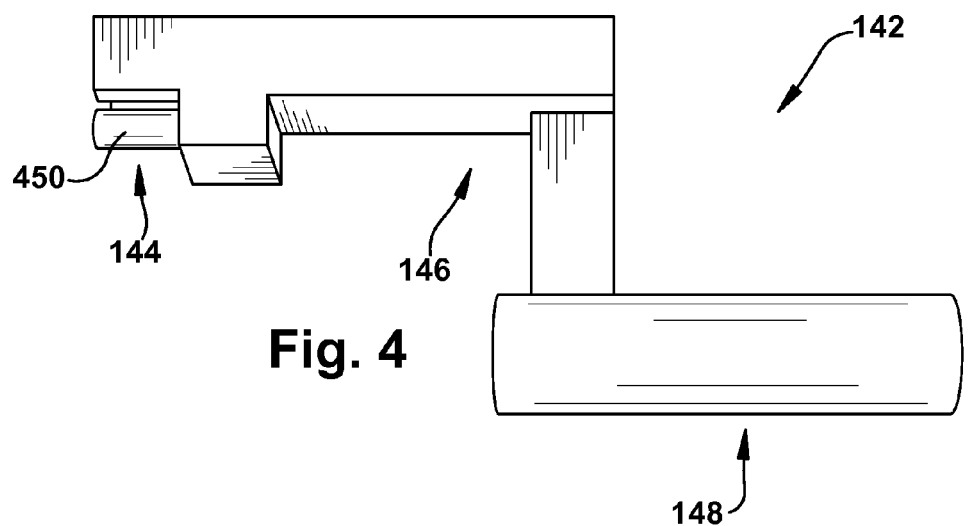
FIG. 4 is a partial perspective top view of the embodiment of FIG. 1.

100. A spacing arm 146 is connected to the attachment structure 144 and extends laterally outward from the post axis 110. A landmark guiding structure 148 is connected to the spacing arm 146, is spaced apart from the center post 102, and embodies at least one of a location and a trajectory for placement of a landmark in association with a patient tissue. The guiding device 142 is shown in magnified solo view in FIG. 4, where details of the attachment structure 144 can be seen. In the depicted attachment structure 144, at least one attachment pin 450 can be configured for placement in a predetermined arrangement with respect to a corresponding pin cavity (352 in FIG. 3) of any implant emulator 124. Optionally, there is an interference/"friction" fit between the attachment pin 450 and the pin cavity 352 which resists removal of the guiding device 142 from the implant emulator 124, though one of ordinary skill in the art can readily provide attachment between the guiding device 142 and any other structure of the apparatus 100 as desired for a particular use environment of the present invention.

While a guiding device 142 could be integrally formed as a unitary, one-piece construct with a particular implant emulator 124 for some use environments of the present invention, it is contemplated that, for most use environments of the present invention, the user will desire to have interchangeable guiding devices 142. That is, a plurality of guiding devices 142, each differing from the others in at least one significant dimension (e.g., length or angle of spacing arm 146; configuration, length, or angle of landmark guiding structure 148; or any other desired difference) could be provided for sequential (or simultaneous, in some instances) use with the apparatus 100. One of ordinary skill in the art could then select the guiding device(s) 142 having the desired significant dimensions or other physical properties for the use environment at hand. Optionally, a first guiding device 142 could be selectively replaceable on the implant emulator 124 (or other structure of the apparatus 100) by a second guiding device 142 having a different significant dimension or other physical property.

As a matter of terminology, a two-dimensional landmark will be described herein as being any pen/pencil mark, bovie burn, pinprick, or other mark which indicates a location, but substantially not a trajectory, of a selected portion of the surface in a user-perceptible form—either via the user's own senses or with the assistance of a perception aid such as, but not limited to, a non-visible light spectrum illuminator. A three-dimensional landmark will be described herein as being any guide pin, Kirschner wire, guidewire, drill bit, or other item which substantially indicates both a location of a selected portion of the surface and a trajectory at which that location is penetrated by the three-dimensional landmark, again in any suitable user-perceptible form. Both two- and three-dimensional landmarks will be referenced collectively herein as "landmarks" and used without discrimination, except where the dimensionality is implicitly or explicitly indicated.

The apparatus 100 of the Figures may be used to dictate at least one of a desired location and a desired trajectory for association of a landmark with an underlying surface, which will be described herein as a patient tissue surface, optionally while concurrently facilitating visualization by the user of at least one physical feature of an implant to be installed at/near the patient tissue surface, without requiring the use of the implant directly at/near the patient tissue surface for the visualization process.

The desired location and/or desired trajectory for the landmark(s) may be preselected in any desired manner. For example, hand calculations and/or a software program may be used to output a desired location and/or trajectory in any suitable format for physical embodiment in the apparatus 100, such as, but not limited to, the specification of predetermined desired positions for each guiding device 142 to be placed into to embody the desired location and/or trajectory. These predetermined guiding device 142 positions could, for example, be based upon preoperative images of the patient tissue acquired in any suitable manner.

One example format for such predetermined guiding device 142 positions could be a group of numerical specifications representing the guiding device to be chosen for use with the apparatus 100 (e.g., through indicating a desired lateral offset related to a particular spacing arm 146 length). Optionally, one or more graduated scales (such as that shown at 140' in FIG. 3) could be used to assist with placement of the guiding device 142 with respect to the patient tissue—in the depicted embodiment, for example, the scaled implant emulator 124c could be placed into a "set" position rotationally about the center post 102 with the aid of the graduated scale 140'. It is also contemplated that some sort of setting stand or setting jig (not shown) may be used to interact with and help set the guiding device 142 or other apparatus 100 structures into predetermined positions/orientations to assist with a landmarking process in a desired manner.

Figure 5:
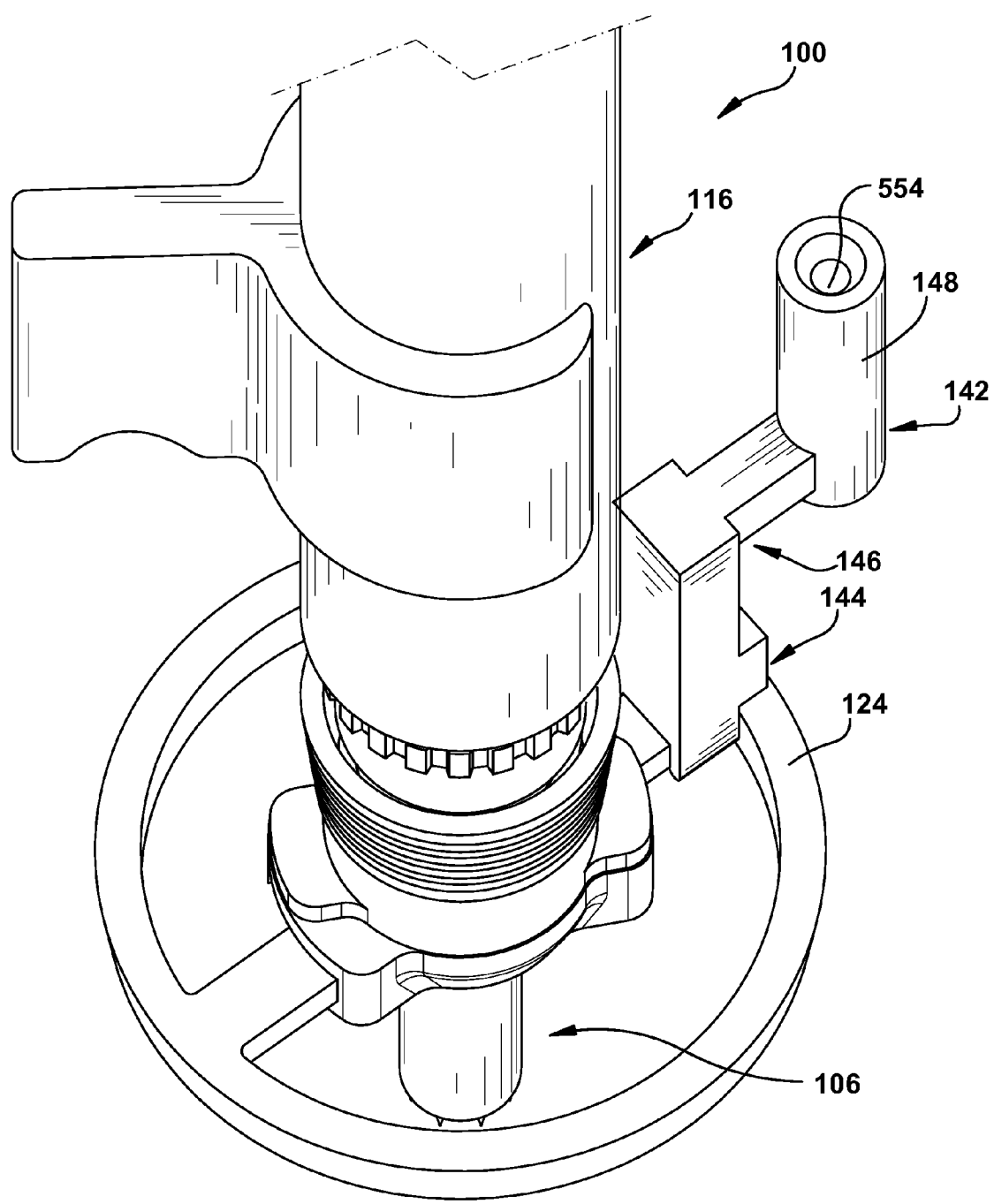
FIG. 5 is a side view of an optional configuration for a component of the embodiment of FIG. 1.

To provide another aspect of the landmarking process, the guiding device 142 can embody a trajectory through use of a passageway extending therethrough, such as the pin guiding bore 554 shown in FIG. 5. An appropriately sized guide pin or other elongate landmark structure (e.g., a drill bit, marking pen/pencil, bovie knife, or the like) can be inserted through the pin guiding bore 554 with the guiding device 142 held in a desired orientation with respect to the patient tissue so that the landmark encounters the patient tissue at a predetermined trajectory. For example, in the embodiment shown in the Figures, the attachment structure 144, spacing arm 146, landmark guiding structure 148, or any other suitable structure of the apparatus 100 can be configured to hold the pin guiding bore 554 at a known orientation with respect to the center post 102 or some other structure of the apparatus. In the depicted embodiment, the guiding device 142 holds the pin guiding bore 554 substantially parallel to, and laterally offset from, the post axis 110. It is contemplated, though, that a suitable static or adjustable guiding device could be provided by one of ordinary skill in the art to assist with guiding a landmark into any desired trajectory for a particular use environment.

Regardless of how the apparatus 100 achieves a desired configuration (e.g., through choice and longitudinal positioning of the implant emulator 124 and/or guiding device 142), the relative positioning of the apparatus with predetermined portions of the patient tissue surface will result in an orientation of the guiding device and/or implant emulator with respect to the patient tissue which dictates at least one of the desired location and the desired trajectory for association of the landmark with the patient tissue and/or aids visualization of the prosthetic implant with respect to the patient tissue. These functions will now be further described with reference to FIGS. 6-9.

It is presumed that, in FIGS. 6-9, the apparatus 100 has been already adjusted into a desired physical configuration for the surgical task being performed. For example, a suitably configured implant emulator 124 has been chosen and attached to the center post 102 via the coupling mechanism 226, and the longitudinal position of the implant emulator (e.g., the distance "A" in FIG. 1) has already been set. This physical configuration may have been assisted through the use of one or more graduated scales 140, 140', which in turn may have been used to transfer intra- or pre-operatively selected settings to the apparatus 100. One suitable preoperative planning method is described in copending U.S. patent application Ser. No. 13/282,550, filed 27 Oct. 2011 and titled "System of Preoperative Planning and Provision of Patient-Specific Surgical Aids", the entire contents of which are incorporated herein by reference. An implant emulator 124 having a particular size and shape can also be selected for use with the apparatus 100 via intra- or pre-operative planning methods. The guiding device 142 has been omitted from FIGS. 6-7 for clarity, but could also be selected for, and/or positioned with respect to, the apparatus through the use of one or more graduated scales 140, 140' and/or intra- or pre-operative planning methods.

Figure 6:
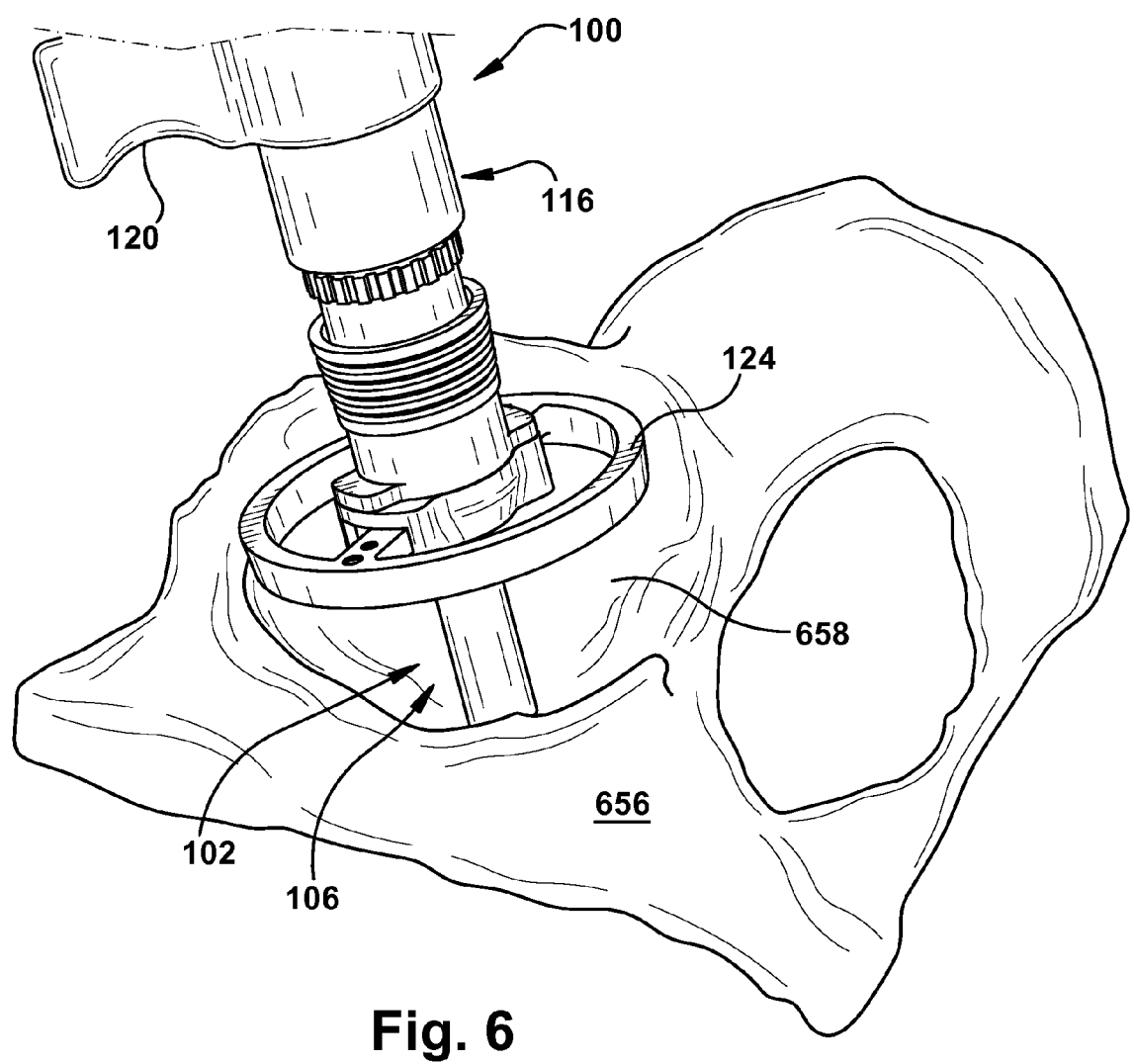
FIG. 6 is a partial side view of the embodiment of FIG. 1 in an example use environment.

In FIG. 6, the apparatus 100 has been placed in close proximity with a patient tissue 656 (represented here as a pelvis model, for clarity). The distal post end 106 has been placed adjacent to, and optionally in contact with, an acetabulum 658 of the patient tissue 656. For example, the user can rest the distal post end 106 in an approximate center of the concave acetabulum 658 "cup". The tissue-engaging feature 112 can assist with maintaining the distal post end 106 in the established contacting relationship as desired by the user by engaging the patient tissue 656.

The position of the apparatus 100 is then manipulated by the user in order to adjust a position of the implant emulator 124 with respect to the acetabulum 658 until the implant emulator achieves a desired visualization position with respect to the patient tissue 656. For example, in the sequence of FIGS. 6-7, the patient tissue 656 is in substantially the same position in both Figures, but the apparatus 100 has been precessed or rotated about the distal post end 106—which remains in substantially the same intersection point with respect to the acetabulum 658 in FIGS. 6 and 7. During adjustment of the position of the apparatus 100, the implant emulator 124 may be adjusted within a concave feature (e.g., the acetabulum 658) in a ball-and-socket type manner. It is also contemplated that the apparatus 100 could stay substantially in the same angular relationship to the acetabulum 658, while the apparatus is being rotated (in place) about the post axis 110 to reflect a substantially rotational (but not precessive or translational) change to the orientation of the implant emulator 124 with respect to the patient tissue 656.

Figure 7:
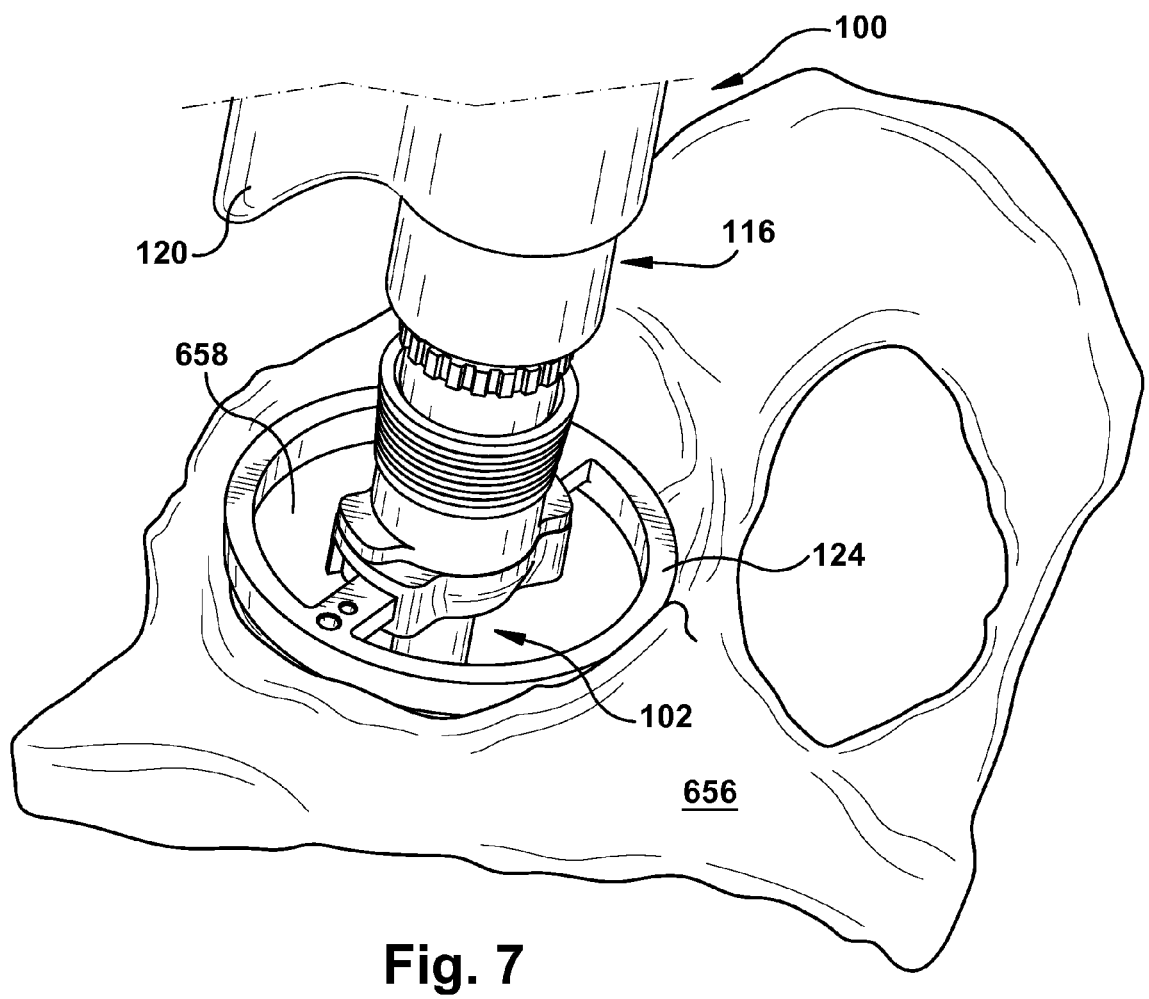
FIG. 7 is a partial side view of the embodiment of FIG. 1 in the example use environment of FIG. 6.

The precession or other movement of the apparatus 100 with respect to the patient tissue 656 moves the implant emulator 124 into a position, as shown in FIG. 7, which aids the user in visualizing how a prosthetic acetabular cup implant corresponding to that particular depicted implant emulator will fit into the acetabulum 658 during a later stage of the surgical procedure. Optionally, the user can replace the in-use implant emulator 124 with one having a different size and/or shape (e.g., chosen from a "library" of implant emulators) in response to the visualization—for example, the user could decide that the initial implant emulator would be too small for that particular patient tissue 656 configuration. The apparatus 100 can then be repositioned as desired to aid the user in visualizing the replacement implant emulator 124 with respect to the patient tissue 656. Visualization of any suitable implant emulator 124 with respect to the patient tissue 656 may aid the user in selecting one of a plurality of available implants (here, acetabular cups) based substantially upon that visual comparison of a position of the implant emulator and/or the distal post end 106 with respect to the patient's acetabulum 658. In other words, once the user is satisfied with the position of the implant emulator 124 with respect to the patient tissue 656, the implant emulator can be correlated with a chosen one of the plurality of available implants. As an example, the user could consult a size marking noted on the particular visualized implant emulator 124 to choose an implant having a corresponding (though not necessarily identical) significant dimension, such as an acetabular cup rim diameter. The user could also or instead refer to the longitudinal distance "A" between the distal post end 106 and the implant emulator 124 to choose an implant having a corresponding (though not necessarily identical) significant dimension, such as an acetabular cup depth.

Figure 8:
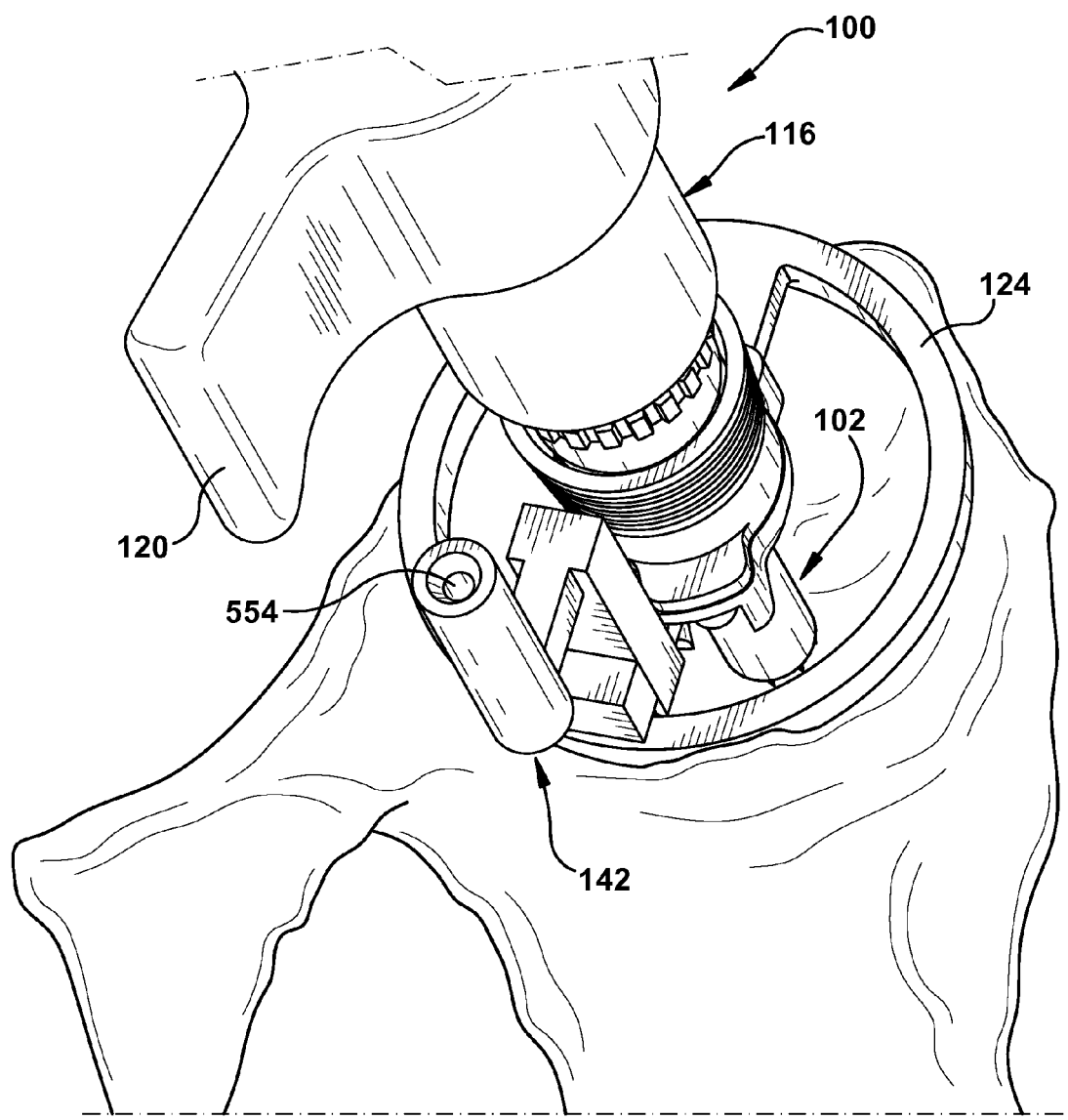
FIG. 8 is a partial side view of the embodiment of FIG. 1 in the example use environment of FIG. 6.
Figure 9:
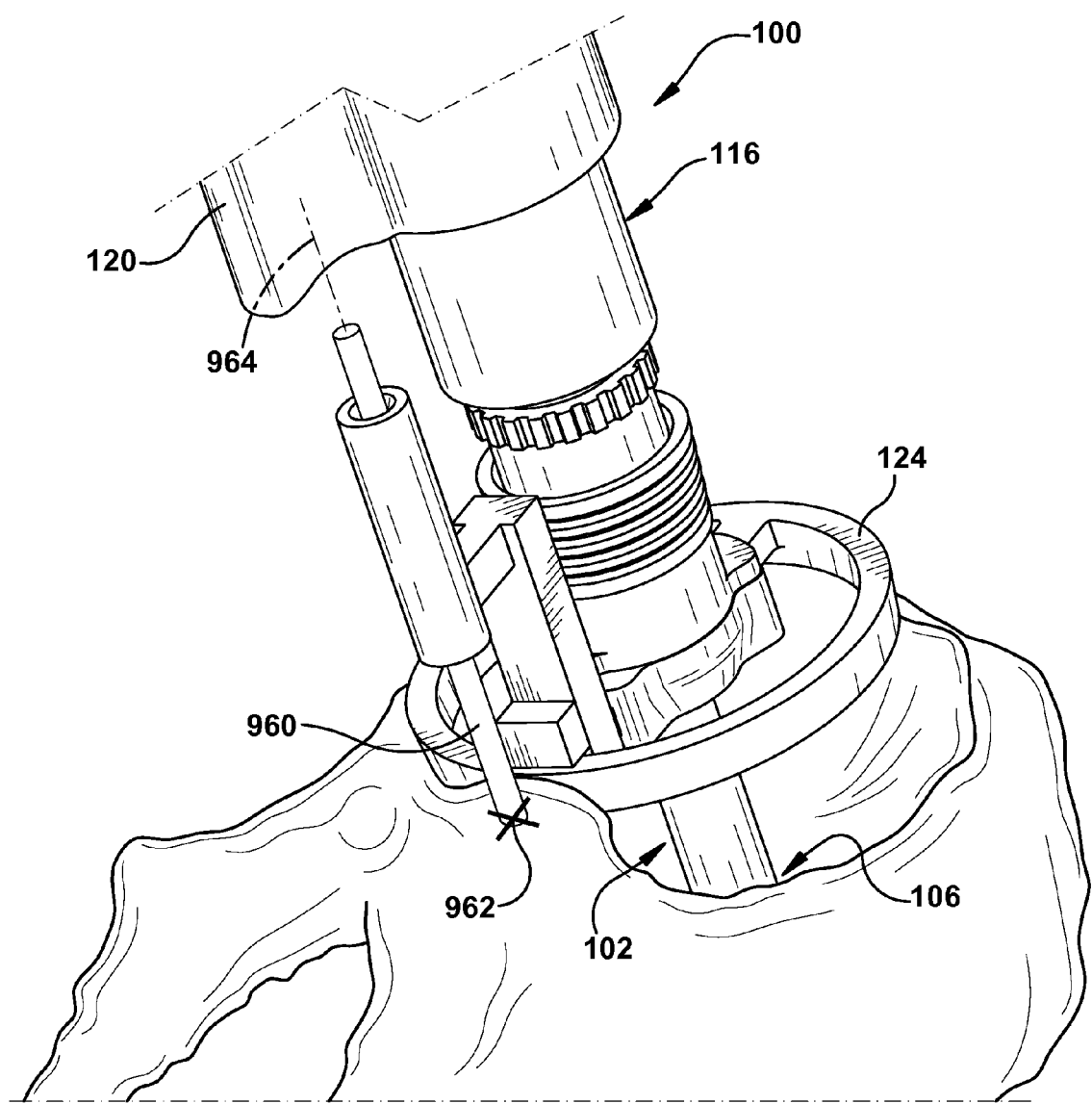
FIG. 9 is a partial side view of the embodiment of FIG. 1 in the example use environment of FIG. 6.

The apparatus 100 can be useful to a surgeon for its visualization properties alone. However, as shown in FIGS. 8-9, the apparatus 100 can also or instead be used to help landmark the patient tissue 656 using a two- or three-dimensional landmark. More specifically, the guiding device 142 could be connected to the implant emulator 124 or another structure of the apparatus 100 before and/or during the surgical procedure, to achieve the configuration shown in FIG. 8. The particular guiding device 142 used for a specific patient tissue 656 could have been chosen from a library of available guiding devices. The apparatus 100 is then manipulated if desired (including a pure rotation about the post axis 110) until the guiding device 142 embodies or "projects" a predetermined location and/or trajectory for placement of a landmark with respect to the patient tissue 656. For example, a desired landmark location could be on a certain area of an acetabular rim, and a desired landmark trajectory could be substantially parallel to, and laterally offset from, the post axis 110 with the apparatus 100 maintained in a desired implant visualization orientation with respect to the acetabulum 658.

Once the guiding device 142 has achieved the desired landmark location and landmark trajectory, in any suitable manner, the guiding device can be used to guide the landmark into that landmark location and landmark trajectory. As shown in FIG. 9, a guide pin 960 has been inserted into a desired landmark location (represented by the "X" at 962) of the patient tissue 656, with the desired landmark trajectory 964 being imparted to the guide pin 960 during guiding of the guide pin through the pin guiding bore 554. Instead of, or in addition to, insertion of the guide pin 960 as a three-dimensional landmark, a marking device or other landmarking aid could be deployed through similar use of the apparatus 100 to provide a two-dimensional landmark (not shown), having no landmark trajectory, at the landmark location 962. As another alternative, a drill bit (not shown) could be directed through the pin guiding bore 554 to penetrate into the patient tissue 656 at a desired landmark location and landmark trajectory, and then removed, leaving behind an aperture in the patient tissue embodying that landmark location and landmark trajectory.

Any suitable numbers and configurations of guiding devices 142 could be used with the apparatus 100 for sequential and/or concurrent landmarking tasks as desired by a user. The apparatus 100, or portions thereof, could be moved after an earlier landmarking task is completed, in order to permit another, later landmarking task using the same guiding device 142 as was used in the earlier landmarking task.

It is also contemplated that structures of the apparatus 100 other than the guiding device 142 could be used for a primary and/or secondary landmarking task of the apparatus. For example, when the center post 102 includes a post lumen 114, the post lumen could be configured to allow passage of at least a portion of a landmark therethrough and thus the post lumen can function as a guiding device. Stated differently, the post lumen 114 could act as a guiding bore for a guide pin, drill bit, marking device, or other landmarking aid therethrough in addition to, or instead of, guiding of a landmark by the laterally located guiding device 142.

As an example, a drill bit could be inserted into the post lumen 114 at the proximal post end 104 and could be guided by the center post 102 to create a guide hole or other aperture in the patient tissue 656 longitudinally adjoining the distal post end 106. This guide hole could be helpful, for instance, when the implant or another surgical instrument "seats" into a hole in the acetabulum 658 during a later surgical task. The length of the center post 102, a key 122, or any other structure could be used as a mechanical stop to limit a depth of insertion of the drill bit into the patient tissue 656. A graduated scale 140 could also or instead be used to inform the user of the depth of insertion of the drill bit into the patient tissue 656 without necessarily interfering with that insertion.

Figure 10:
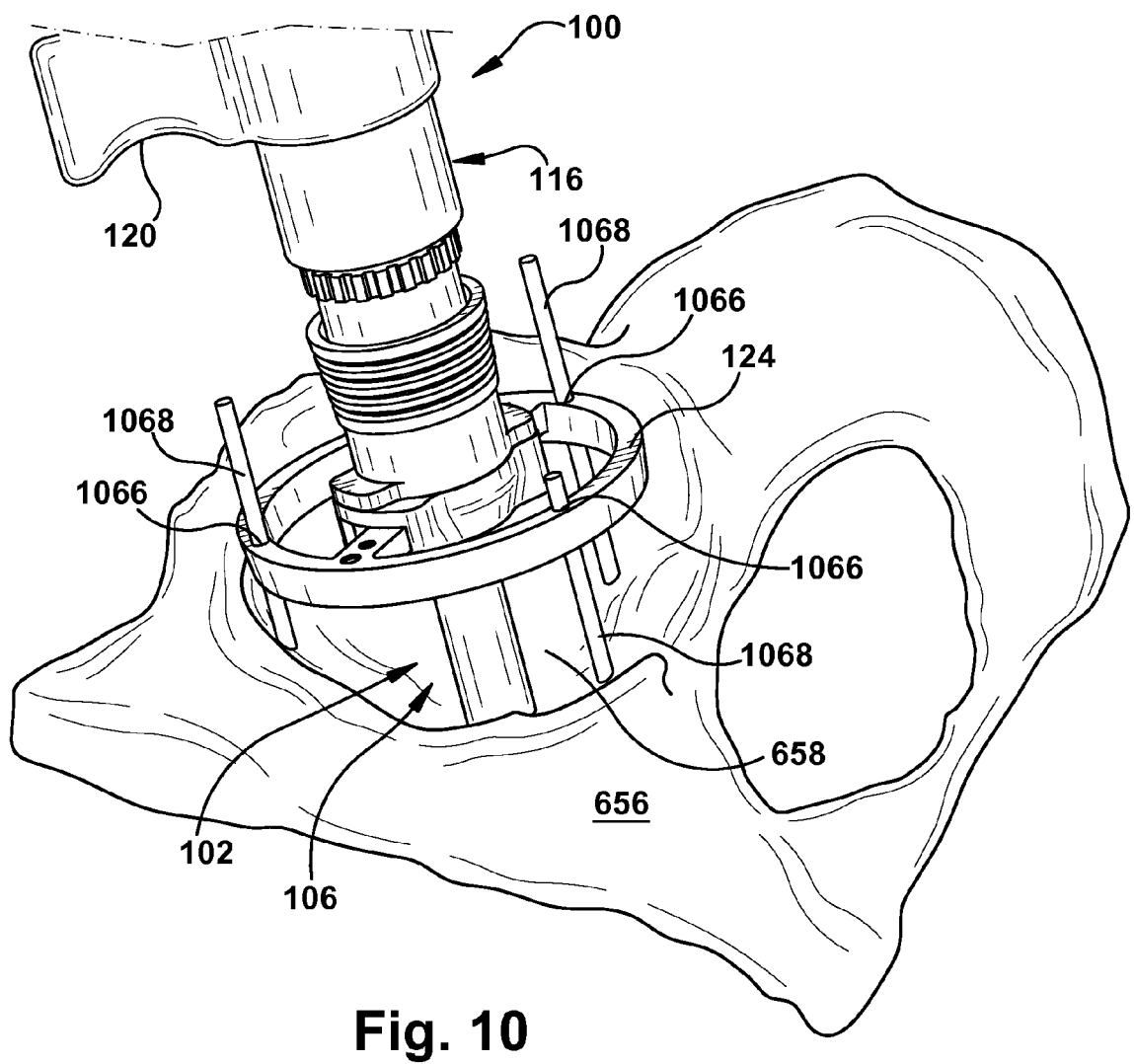
FIG. 10 is a partial side view of the embodiment of FIG. 1 in an example use environment.

FIG. 10 depicts an optional configuration of the apparatus 100 of FIG. 1, in which at least one aperture 1066 (three shown) is provided in the implant emulator 124 or another structure of the apparatus 100. Each aperture 1066 may be configured to receive an indicator rod 1068 which communicates spatial information to the user and/or embodies a "setting" of the apparatus 100 to assist the user with placing the apparatus 100 into a desired position for at least one of a visualization task and a landmarking task. Each indicator rod 1068 may be movably held within a corresponding aperture 1066 with a predetermined length of the rod extending from the implant emulator 124 toward the patient tissue 656. For example, there could be a friction/interference fit between the indicator rods 1068 and the apertures 1066, a set screw could be used to hold the rods in place, or any other retaining scheme could be provided by one of ordinary skill in the art. It is contemplated that a plurality of apertures 1066 could be provided to the apparatus 100, with only a subset of those apertures receiving indicator rods 1068 for a particular surgical use of the apparatus.

The predetermined length(s) of the indicator rod(s) 1068 may be provided, for example, by a preoperative planning system/software which directs the user to select certain lengths of rods from a library and/or to insert rods to a certain "depth" (e.g., guided by a graduated scale marked along the rod) in the apertures 1066. When the apparatus 100 is oriented respective to the patient tissue 656 such that each indicator rod 1068 comes into a predetermined relationship with the patient tissue 656 (e.g., lightly contacting a surface of the acetabulum 658), the user then becomes aware that a desired orientation of the apparatus with respect to the patient tissue has been achieved. This awareness could arise via, for example, a simple visual and/or tactile observation, but it is also contemplated that some mechanical, electrical, and/or other non-human means could be used to indicate the positional achievement. For example, a light could come on when contact between all indicator rods 1068 and the patient tissue 656 causes an electrical circuit to be completed. This may be particularly helpful if surgical exposure obstructs a user's ability to directly visualize some portion of the patient tissue 656.

Instead of, or in addition to, the depicted indicator rods 1068 and apertures 1066, it is contemplated that any desired arrangement of orienting structures could be provided to the apparatus 100 by one of ordinary skill in the art to assist the user with bringing the apparatus into a desired position with respect to the patient tissue 656 by contacting portions of the patient tissue other than those to be landmarked. However, it is also contemplated that the orienting structures (e.g., the indicator rods 1068 and/or apertures 1066) may be used to assist with at least one of a landmarking and/or visualizing task directly, as well.

Once the implant emulator 124 has been used for a visualization task and/or one or more structures of the apparatus 100 (e.g., the guiding device 124 and/or a post lumen 114) have been used to assist with a landmarking task, the apparatus 100 can be removed from the patient tissue 656 and the surgical tasks can proceed apace, optionally using the apparatus-placed guide pin 960 as an ongoing physical landmark or reference point. The removed apparatus 100, or portions thereof, may be disposed of when configured for one-time use or may be sterilized for reuse.

The above description presumes that the apparatus 100, or components thereof, are provided, adjusted, and/or otherwise configured responsive to outputs from preoperative software (e.g., when a graduated scale 140 value is provided) and/or the knowledge/skill of the user (e.g., when an orientation and/or position is "eyeballed" or chosen by the user in real-time with reference to the patient tissue 656). However, it is contemplated that one or more of the manipulable structures of the apparatus 100 may be configured by the user with the assistance of a physical model (not shown) of the native tissue, such as those disclosed in copending U.S. patent application Ser. No. 13/463,075, filed 3 May 2012 and titled "System of Preoperative Planning and Provision of Patient-Specific Surgical Aids", the entire contents of which are incorporated herein by reference. For example, a user could manipulate the apparatus 100 into a desired position with respect to a physical model before or during the surgical procedure and then configure one or more indicator rods 1068, with the assistance of that physical model, to help transfer the desired position of the apparatus to the patient tissue 656 corresponding to that physical model.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described apparatus 100 are merely illustrative; one of ordinary skill in the art could readily determine any number or type of components, sequences of steps, or other means/options for guiding a landmark in a manner substantially similar to those shown and described herein. Any of the described structures and components could be integrally formed as a single piece or made up of separate sub-components, with either of these formations involving any suitable stock or bespoke components and/or any suitable material or combinations of materials. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. The implant emulator 124 could be provided to, and located longitudinally upon, the center post 102 in any suitable manner, including as a one-piece unitary construct which does not allow for a change of the longitudinal spacing between the implant emulator and the distal post end 106. While a one-dimensional (along a line) "landmark" is nonsensical for most use environments of the present invention, such a one-dimensional landmark could be provided for an appropriate use environment similarly to the two- (location only) and three- (location and trajectory) dimensional landmarks discussed herein. At least a portion of the apparatus 100 could be patient specific (e.g., a patient-specific guiding device 124) for use with remaining stock/generic structures of the apparatus. The guiding device 142 could be provided to the center post 102 and/or the implant emulator 124 in any suitable manner, including as a one-piece unitary construct which does not allow for a change of position of the guiding device with respect to one or more other structures of the apparatus 100. The apparatus 100 could be used with any type of landmark, e.g., two- or three-dimensional, and temporary, semi-permanent, or permanent. The apparatus 100 could be at least partially disposable or intended for one-time use, possibly by including a sacrifice feature (not shown) rendering the instrument unusable after an initial use—this may be particularly helpful in a medical use environment if the apparatus is not intended for repeat sterilization and reuse. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An apparatus for aiding visualization of a prosthetic implant and concurrently landmarking a patient tissue, the apparatus comprising:
    a center post having proximal and distal post ends longitudinally separated by a post body, the post body defining a post axis coaxially therewith;
    an implant emulator embodying a reference feature of a prosthetic implant, the implant emulator being carried on an outer surface of the center post at a predetermined longitudinal spacing from the distal post end; and
    a guiding device removably and directly attached to the implant emulator, the guiding device including an attachment structure attached to the implant emulator, a spacing arm connected to the attachment structure and extending laterally outward from the post axis, and a landmark guiding structure connected to the spacing arm, spaced apart from the center post, and embodying at least one of a location and a trajectory for placement of a landmark.

2. The apparatus of claim 1, wherein the distal post end includes at least one tissue-engaging feature.

3. The apparatus of claim 1, wherein the predetermined longitudinal spacing is a first predetermined longitudinal spacing and the implant emulator is selectively longitudinally movable to a second predetermined longitudinal spacing along the center post.

4. The apparatus of claim 1, wherein a combination of a significant dimension of the implant emulator and the predetermined longitudinal spacing corresponds directly to a significant dimension and a longitudinal measurement of an available prosthetic implant.

5. The apparatus of claim 1, including a post lumen extending through the post body between the proximal and distal post ends coaxially with the post axis.

6. The apparatus of claim 5, wherein the landmark is a first landmark and the post lumen is a guiding device for a second landmark inserted therethrough.

7. The apparatus of claim 1, wherein the implant emulator is a first implant emulator and including a coupling mechanism removably connecting the first implant emulator to the center post, the coupling mechanism being manipulable to removably connect a second implant emulator, differing in a significant dimension from the first implant emulator, to the center post in place of the first implant emulator.

8. The apparatus of claim 7, wherein the first and second implant emulators have substantially the same physical configuration but differ in scale from one another.

9. The apparatus of claim 1, wherein the guiding device is a first guiding device and including a second guiding device, differing in a significant dimension from the first guiding device, the first guiding device being selectively replaceable on the implant emulator by the second guiding device.

10. The apparatus of claim 1, wherein a position of at least one of the implant emulator and the guiding device with respect to the center post is established via the use of a graduated scale of the apparatus.

11. The apparatus of claim 1, including at least one aperture configured to receive an indicator rod, the indicator rod communicating spatial information to assist with placing the apparatus into a desired position for at least one of a visualization task and a landmarking task.

12. An apparatus for trialing a portion of an acetabular cup and concurrently placing at least one landmark at an acetabular surgical site, the apparatus comprising:
    a center post having proximal and distal post ends longitudinally separated by a post body, the post body defining a post axis coaxially therewith;
    a cup emulator representing only a rim portion of an acetabular cup, the cup emulator being carried on an outer surface of the center post at a predetermined longitudinal spacing from the distal post end, the cup emulator being coaxial with the post axis; and
    a pin guide removably and directly attached to the cup emulator, the pin guide including an attachment structure attached to the cup emulator, a spacing arm connected to the attachment structure and extending laterally outward from the post axis, and a pin guiding bore connected to the spacing arm, spaced apart from the center post, and embodying at least one of a location and a trajectory for placement of a landmark with respect to the center post and the cup emulator.

13. The apparatus of claim 12, wherein the distal post end includes at least one tissue-engaging feature for placement within an acetabulum of a patient.

14. The apparatus of claim 12, wherein the predetermined longitudinal spacing is a first predetermined longitudinal spacing and the cup emulator is selectively longitudinally movable to a second predetermined longitudinal spacing along the center post.

15. The apparatus of claim 12, wherein a combination of a significant dimension of the cup emulator and the predetermined longitudinal spacing corresponds directly to a significant dimension and a longitudinal measurement of an available acetabular cup.

16. The apparatus of claim 12, wherein a user chooses one of a plurality of available acetabular cups based substantially upon a visual comparison of a position of the cup emulator and of the distal post end with respect to a patient's acetabulum at the acetabular surgical site.

17. The apparatus of claim 12, including a post lumen extending through the post body between the proximal and distal post ends coaxially with the post axis.

18. The apparatus of claim 17, wherein the landmark is a first landmark and the post lumen is a guiding device for a second landmark inserted therethrough.

19. The apparatus of claim 18, wherein the second landmark is a drill which is configured to create a guide hole in the acetabulum longitudinally adjoining the distal post end.

20. The apparatus of claim 12, wherein the cup emulator is a first cup emulator and including a coupling mechanism removably connecting the first cup emulator to the center post, the coupling mechanism being manipulable to removably connect a second cup emulator, differing in a significant dimension from the first cup emulator, to the center post in place of the first cup emulator.

21. The apparatus of claim 20, wherein the first and second cup emulators have substantially the same physical configuration but differ in scale from one another.

22. The apparatus of claim 12, wherein the pin guide is a first guiding device and including a second guiding device, differing in a significant dimension from the first guiding device, the first guiding device being selectively replaceable on the cup emulator by the second guiding device.

23. The apparatus of claim 12, wherein a position of at least one of the cup emulator and the pin guide with respect to the center post is established via the use of a graduated scale of the apparatus.

24. The apparatus of claim 12, including at least one aperture configured to receive an indicator rod, the indicator rod communicating spatial information to assist with placing the apparatus into a desired position for at least one of a visualization task and a landmarking task.

25. A method of aiding visualization of a prosthetic implant and concurrently landmarking the surgical site, the method comprising the steps of:
providing a device comprising:
a center post having proximal and distal post ends longitudinally separated by a post body, the post body defining a post axis coaxially therewith,
an implant emulator embodying a reference feature of a prosthetic implant, the implant emulator being carried on an outer surface of the center post at a predetermined longitudinal spacing from the distal post end, and
a guiding device removably attached to the implant emulator, the guiding device including an attachment structure attached to the implant emulator, a spacing arm connected to the attachment structure and extending laterally outward from the post axis, and a landmark guiding structure connected to the spacing arm, spaced apart from the center post, and embodying at least one of a location and a trajectory for placement of a landmark;
placing the distal post end in contact with a patient tissue at the surgical site;
adjusting a position of the implant emulator with respect to the patient tissue;
placing the implant emulator in a desired visualization position with respect to the patient tissue; and
with the implant emulator maintained in the desired visualization position, placing a landmark into at least one of a desired landmark location and a desired landmark trajectory with respect to the patient tissue with the aid of at least one of the post body and the landmark guiding structure.

26. The method of claim 25, wherein the step of placing the distal post end in contact with a patient tissue at the surgical site includes the step of resisting motion of the distal post end with respect to the patient tissue by engagement of the patient tissue with at least one tissue-engaging feature of the distal post end.

27. The method of claim 25, wherein the predetermined longitudinal spacing is a first predetermined longitudinal spacing and including the step of selectively longitudinally moving the implant emulator to a second predetermined longitudinal spacing along the center post.

28. The method of claim 25, including the step of corresponding a combination of a significant dimension of the implant emulator and the predetermined longitudinal spacing directly to a significant dimension and a longitudinal measurement of an available prosthetic implant.

29. The method of claim 25, including the step of choosing one of a plurality of available acetabular cups based substantially upon a visual comparison of a position of the implant emulator with respect to the patient tissue.

30. The method of claim 25, including a post lumen extending through the post body between the proximal and distal post ends coaxially with the post axis.

31. The method of claim 30, wherein the landmark is a first landmark inserted into at least one of a desired first landmark location and a desired first landmark trajectory with respect to the patient tissue with the aid of a chosen one of the post lumen and the landmark guiding structure and including the step of, with the implant emulator maintained in the desired visualization position, placing a second landmark into at least one of a desired second landmark location and a desired second landmark trajectory with respect to the patient tissue with the aid of the other one of the post lumen and the landmark guiding structure.

32. The method of claim 25, wherein the implant emulator is a first implant emulator and the step of providing a device includes the step of removably connecting the first implant emulator to the center post with a coupling mechanism, the method including the step of manipulating the coupling mechanism to removably connect a second implant emulator, differing in a significant dimension from the first implant emulator, to the center post in place of the first implant emulator.

33. The method of claim 32, wherein the first and second implant emulators have substantially the same physical configuration but differ in scale from one another.

34. The method of claim 25, wherein the guiding device is a first guiding device and the step of providing a device includes the step of providing a second guiding device, differing in a significant dimension from the first guiding device, the method including the step of selectively replacing the first guiding device on the implant emulator by the second guiding device.

35. The method of claim 25, wherein the step of adjusting a position of the implant emulator with respect to the patient tissue includes the step of precessing the center post about an intersection point between the distal post end and the patient tissue.

36. The method of claim 25, wherein the step of adjusting a position of the implant emulator with respect to the patient tissue includes the step of adjusting a position of the implant emulator within a concave feature of the patient tissue in a ball-and-socket manner.

37. The method of claim 25, wherein the step of adjusting a position of the implant emulator with respect to the patient tissue includes the step of rotating the implant emulator around the post axis.

38. The method of claim 25, wherein the landmark is a drill which creates a guide hole in the patient tissue at a location dictated by at least one of the post body and the landmark guiding structure.

39. The method of claim 25, including the step of establishing a position of at least one of the implant emulator and the guiding device with respect to the center post via the use of a graduated scale of the apparatus.

40. The method of claim 25, including the steps of:
providing at least one aperture to the device;
receiving an indicator rod in the at least one aperture;
communicating spatial information to a user with the indicator rod; and
with the communicated spatial information, assisting with placing the device into a desired position for at least one of a visualization task and a landmarking task.

* * * * *